(12) United States Patent
Cullinan et al.

(10) Patent No.: US 6,432,982 B1
(45) Date of Patent: Aug. 13, 2002

(54) BENZOTHIOPHENES, AND FORMULATIONS AND METHODS USING SAME

(75) Inventors: George Joseph Cullinan, Trafalgar; Kennan Joseph Fahey, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/783,160

(22) Filed: Jan. 14, 1997

Related U.S. Application Data

(60) Provisional application No. 60/011,990, filed on Feb. 21, 1996.

(51) Int. Cl.[7] ............... A61K 31/445; C07D 409/12
(52) U.S. Cl. ............... 514/324; 514/212; 514/238.8; 514/422; 514/443; 540/536; 540/609; 544/146; 546/202; 548/525; 548/527; 549/49; 549/52
(58) Field of Search ............... 540/536, 609; 548/525, 527; 549/49, 52; 544/146; 514/212, 238.8, 324, 422, 443

(56) References Cited

U.S. PATENT DOCUMENTS

| | | | |
|---|---|---|---|
| 3,293,263 A | 12/1966 | Lednicer | 260/326.5 |
| 3,320,271 A | 5/1967 | Lednicer | 260/307 |
| 3,862,232 A | 1/1975 | Lednicer | 260/570.7 |
| 4,133,814 A | 1/1979 | Jones et al. | 260/326.5 |
| 4,358,593 A | 11/1982 | Jones et al. | 546/202 |
| 4,380,635 A | 4/1983 | Peter | 546/202 |
| 4,418,068 A | 11/1983 | Jones | 414/267 |
| 5,223,510 A | 6/1993 | Gubin et al. | 514/299 |
| 5,470,854 A | 11/1995 | von Angerer et al. | 514/233.5 |
| 5,472,962 A | 12/1995 | Koizumi et al. | 514/233.5 |
| 5,482,949 A | 1/1996 | Black et al. | 514/324 |
| 5,484,798 A | 1/1996 | Bryant et al. | 514/324 |
| 5,510,357 A | 4/1996 | Palkowitz | 514/324 |
| 5,532,382 A | 7/1996 | Carlson et al. | 549/57 |

FOREIGN PATENT DOCUMENTS

| | | | |
|---|---|---|---|
| EP | 0 062 503 | 10/1982 | |
| EP | 0 516 257 A1 | 12/1992 | C07D/307/80 |
| EP | 0 584 952 A1 | 3/1994 | A61K/31/445 |
| EP | 0 617 030 A1 | 9/1994 | |
| EP | 0 641 791 A1 | 3/1995 | C07D/333/56 |
| EP | 0729964 | * 2/1996 | C07F/9/6553 |
| EP | 0731100 | * 3/1996 | C07D/333/56 |
| EP | 0731101 | * 3/1996 | C07D/333/56 |
| EP | 0747376 | * 5/1996 | C07D/333/56 |
| GB | 1138163 | 12/1968 | C07D/63/22 |
| WO | WO95/10513 | 4/1995 | |
| WO | 9640098 | * 12/1996 | A61K/31/135 |

OTHER PUBLICATIONS

Oparil "Hypertension in postmenopausal women . . . " EMBASE 95283951 (1995).*
Robinson et al. "Reversal of the antitumor effects of tamoxifen by progesterone . . . " BIOSIS 85006817 (1987).*
Jeng et al. "Estrogenic potential of progestins . . . " SciSEARCH 11952719 (1992).*
Cameron et al. "Benzothiophenes and related compounds as estrogen agonists" CA 123:143630 (1995) 117 RN compounds.*
Dodge, et al. "The chemical probe for the estrogen receptor synthesis of the 3H–isotopomer of raloxifene", Chemical Abstracts, vol. 122, No. 17, Apr. 24, 1995, CA122: 2138839.
Jones, et al., *J. Med. Chem.*, 35: 931–938 (1992).
Crenshaw, et al., *J. Med. Chem.*, 14: 1185–1190 (1971).
Lednicer, et al., *J. Med. Chem.* 8:52–57 (1964).

* cited by examiner

*Primary Examiner*—Ceila Chang
(74) *Attorney, Agent, or Firm*—Gary M. Birch; Jerry F. Janssen

(57) ABSTRACT

The invention provides novel benzothiophenes of the formula:

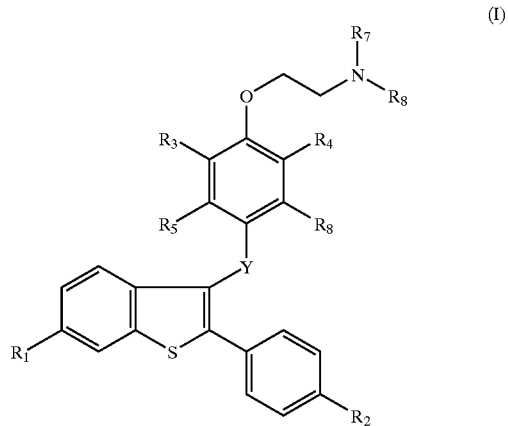

wherein $R_1$ is —H, —OH, —O($C_1$–$C_4$ alkyl), —O—CO ($C_1$–$C_6$ alkyl), —$OSO_2$($C_4$–$C_6$ alkyl, or —OCOAr where Ar is optionally substituted phenyl; $R_2$ is —H, —OH, —Cl, —Br, —O($C_1$–$C_4$ alkyl), —OCO($C_1$–$C_6$ alkyl), —$OSO_2$ ($C_4$–$C_6$ alkyl, or —OCOAr where Ar is optionally substituted phenyl; $R_3$ is —H, —F, —Cl, —($C_1$–$C_4$ alkyl), —CN, or —O($C_1$–$C_3$ alkyl); $R_4$ is —H, —F, —Cl, —($C_1$–$C_4$ alkyl), —CN or —O($C_1$–$C_3$ alkyl); $R_5$ is —H, —F, —Cl, —($C_1$–$C_4$ alkyl), or —O($C_1$–$C_3$ alkyl); and $R_6$ is —H, —F, —Cl, —($C_1$–$C_4$ alkyl), or —O($C_1$–$C_3$ alkyl); with the provisos that $R_3$, $R_4$, $R_5$ and $R_6$ can not all be hydrogen, and that when one of $R_3$, $R_4$, $R_5$ or $R_6$ is $C_1$–$C_4$ alkyl, no more than two of $R_3$, $R_4$, $R_5$ and $R_6$ can be hydrogen; Y is —CO—, —CHOH—, or —$CH_2$—; $R_7$ and $R_8$ are independently $C_1$–$C_4$ alkyl or combine to form, with the nitrogen to which they are attached, 1-piperidinyl, 1-pyrrolidinyl, 1-hexamethyleneimino, or morpholino; or a pharmaceutically acceptable salt thereof. The present invention further provides pharmaceutical compositions containing compounds of formula I, optionally containing estrogen opr progestin, and the use of such compounds alone, or in combination with estrogen or progestin or alleviating the symptoms of post-menopausal syndrome, particularly osteoporosis, cardiovascular related pathological conditions, and estrogen-dependent cancer.

11 Claims, No Drawings

BENZOTHIOPHENES, AND FORMULATIONS AND METHODS USING SAME

This application claims benefit of provisional application 60/011,990 filed Feb. 21, 1996.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: Osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of some or all of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Smooth muscle cell proliferation plays an important role in diseases such as atherosclerosis and restenosis. Vascular restenosis after percutaneous transluminal coronary angioplasty (PTCA) has been shown to a tissue response characterized by an early and late phase. The early phase occurring hours to days after PTCA is due to thrombosis with some vasospasms while the late phase appears to be dominated by excessive proliferation and migration of vascular aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the re occlusion of coronary arteries following PTCA, laser angioplasty, and arterial bypass graft surgery. See: "Intimal Proliferation of Smooth Muscle Cells as an Explanation for Recurrent Coronary Artery Stenosis after Percutaneous Transluminal Coronary Angioplasty", Austin et al., *Journal of the American College of Cardiology*, 8,: 369–375 (August 1985).

Vascular restenosis remains a major long term complication following surgical intervention of blocked arteries by PTCA, atherectomy, laser angioplasty, and arterial bypass graft surgery. In about 35% of the patients who undergo PTCA, re occlusion occurs within 3 to 6 months after the procedure. The current strategies for treating vascular restenosis include mechanical intervention by devices such as agents or pharmacologic therapies including heparin, low molecular weight heparin, coumarin, aspirin, fish oil, calcium antagonists, steroids, and prostacyclin. These strategies have failed to curb the re occlusion rate and have been ineffective for the treatment and prevention of vascular restenosis. See: "Prevention of Restenosis after Percutaneous Transluminal Coronary Angioplasty: The Search for a 'Magic Bullet'", Hermans et al., *American Heart Journal*, 122,: 171–187 (July 1991).

In the pathogenesis of restenosis, excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use compounds as smooth aortal muscle cell proliferation inhibitors and, thus inhibitors of restenosis.

SUMMARY OF THE INVENTION

The invention provides novel benzothiophenes of the formula (I):

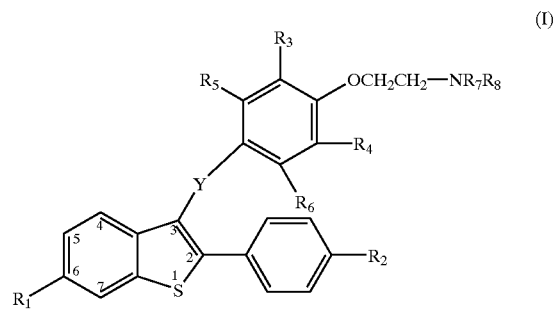

(I)

$R_1$ is —H, —OH, —O($C_1$-$C_4$ alkyl), —O—CO($C_1$-$C_6$ alkyl), —OSO$_2$($C_4$-$C_6$ alkyl), or —OCOAr where Ar is optionally substituted phenyl;

$R_2$ is —H, —OH, —O($C_1$-$C_4$ alkyl), —OCO($C_1$-$C_6$ alkyl), —OSO$_2$($C_4$-$C_6$ alkyl), —OCOAr where Ar is optionally substituted phenyl, —Cl, or —Br;

$R_3$ is —H, —F, —Cl, —$C_1$-$C_4$ alkyl, —CN, or —O($C_1$-$C_3$ alkyl);

$R_4$ is —H, —F, —Cl, —$C_1$-$C_4$ alkyl, —CN, or —O($C_1$-$C_3$ alkyl);

$R_5$ is —H, —F, —Cl, $C_1$-$C_4$ alkyl, or —O($C_1$-$C_3$ alkyl);

$R_6$ is —H, —F, —Cl, $C_1$-$C_4$ alkyl, or —O($C_1$-$C_3$ alkyl);

with the proviso that $R_3$, $R_4$, $R_5$, and $R_6$ can not all be hydrogen;

Y is —CO—, —CHOH—, or —CH$_2$—;

$R_7$ and $R_8$ each are independently $C_1$-$C_4$ alkyl or combine to form, with the nitrogen to which they are attached, 1-piperidinyl, 1-pyrrolidinyl, 1-hexamethyleneimino, or morpholino;

or a pharmaceutically acceptable salt thereof.

A preferred embodiment of this invention is the compound where $R_1$ and $R_2$ each are hydroxy, $R_5$ and $R_6$ each are hydrogen; $R_3$ and $R_4$ each are methyl; and $R_7$ and $R_8$ form a piperidinyl moiety, viz., [2-(4-hydroxyphenyl)-6-hydroxybenzo[b]thien-3-yl][4-[2-(1-piperidinyl)ethoxy]-3,5-dimethylphenyl] methanone and its hydrochloride salt.

A most preferred embodiment of this invention is the compound where $R_1$ and $R_2$ each are hydroxy, $R_4$, $R_5$, and $R_6$ each are hydrogen; $R_3$ is fluoro; and $R_7$ and $R_8$ form a piperidinyl moiety, viz., [2-(4-hydroxyphenyl)-6-hydroxybenzo[b]thien-3-yl][4-[2-(1-piperidinyl)ethoxy]-3-fluorophenyl]methanone, and its hydrochloride salt.

The present invention also relates to pharmaceutical acceptable compositions comprising a compound of formula I and pharmaceutically acceptable diluent or carrier.

Included within the scope of compounds of formula I are isomers of asymmetric center.

The present invention further relates to pharmaceutical compositions containing compounds of formula I, optionally containing estrogen or progestin, and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example 17β-estradiol, estrone, conjugated estrogen (Premarin®), equine estrogens, 17β-ethynyl estradiol, and the like. As used herein, the term "progestin" includes compounds having progestational activity such as, for example, progesterone, norethylnodrel, nongestrel, megestrol acetate, norethindrone, and the like.

DETAILED DESCRIPTION OF THE INVENTION

The current invention relates to the discovery of a new series of benzo[b]thiophenes shown in formula I. These compounds are useful for inhibiting pathological conditions associated with post-menopausal syndrome.

The term "inhibit" includes its generally accepted meaning which includes prohibiting, preventing, restraining, and slowing, stopping, or reversing progression, severity, or a resultant symptom. As such, the methods include both medical therapeutic and/or prophylactic administration, as appropriate.

General terms used in the description of compounds herein described bear their usual meanings. For example, "$C_1$–$C_4$ alkyl" refers to straight or branched aliphatic chains of 1 to 4 carbon atoms including methyl, ethyl, propyl, iso-propyl, n-butyl, and the like; and "$C_1$–$C_6$ alkyl" encompasses the groups included in the definition of "$C_1$–$C_4$ alkyl" in addition to groups such as pentyl, iso-pentyl, hexyl, and the like. The exception to this terminology is in the case of the sulfonyl derivatives, i.e., "—O—$SO_2$—($C_4$–$C_6$ alkyl)", where it is meant to be only; n-butyl, n-pentyl, or n-hexyl.

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, or tri(chloro or fluoro)methyl. "$C_1$–$C_3$ alkoxy" refers a $C_1$–$C_3$ alkyl group attached through an oxygen bridge such as , methoxy, ethoxy, n-propoxy, iso-propoxy.

The compounds of the present invention, i.e., compounds of formula I, may be prepared essentially as described in the U.S. Pat. No. 4,133,814, issued Jan. 9, 1979, U.S. Pat. No. 4,358,593, issued Nov. 9, 1982, U.S. Pat. No. 4,418,068, issued Nov. 29, 1983, U.S. Pat. No. 5,393,763 issued Feb. 28, 1995, and U.S. Pat. No. 5,482,949 issued Jan. 9, 1996 each of which is incorporated by reference.

Briefly, compounds of formula II may be acylated at the 3-position of the benzothiophene nucleus with an activated carboxyl moieties of the compounds of formula III under standard Friedel-Crafts conditions. In general, the acylating conditions would be the use of a Lewis acid such as, $AlCl_3$, $BF_3$, and the like, in an appropriate solvent such a halogenated hydrocarbon, at temperatures from 0–100° C. The activated carboxyl moieties of the compounds of formula III are acyl halides, mixed anhydrides, and the like, preferred would be the acid chloride. The compounds of formula II may be prepared in accordance with the methods described in U.S. Pat. No. 4,133,814. It would be understood to those skilled in the art of organic chemistry that the ligands $R_1$ and $R_2$ must be compatible with the acylating conditions to form the compounds of formula I, thus a preferred intermediate would where $R_1$ and $R_2$ are —OMe. The activated carboxyls of the compounds of formula III may be prepared from commercially available carboxylic acids or methods known in the art, with agents such as thionyl chloride.

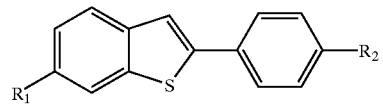

II where $R_1$ and $R_2$ have their previous meanings.

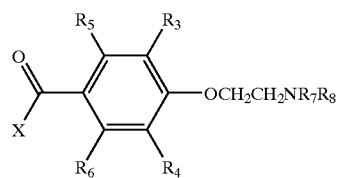

III and $R_3$, $R_4$, $R_5$, $R_6$, $R_7$, and $R_8$ have their previous meanings, and X is an activating moiety such as —Cl, Br, OAc, and the like.

Other compounds of formula I where $R_1$ and $R_2$ are esters or sulfonates can be derived from de-methylating the dimethoxy compound with $AlCl_3$, $BCl_3$, etc., and acylating with the appropriate acyl or sulfonyl moiety.

An alternate method of preparing the compounds of formula I, especially preferred for the preparation of the preferred compounds of this invention, would be to acylate the 3-position on a compound of formula II with a compound of formula IV, using standard Friedel-Crafts conditions, to form the compounds of formula V. The 4-OMe group of the benzoyl moiety may be selectively removed using NaSEt to form the compounds of formula VI. The compounds of formula VI may O-alkylated with the compounds of formula VII with an inorganic base such $K_2CO_3$, $Cs_2CO_3$, and the like, to form the final compounds of formula I.

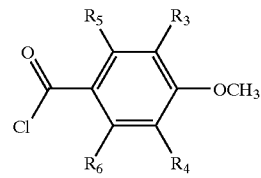

IV where $R_3$, $R_4$, $R_5$, and $R_6$ have their previous meanings.

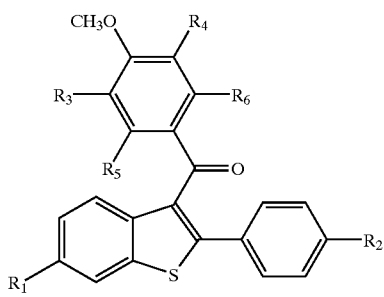

where $R_1$, $R_2$, $R_3$, $R_4$, $R_5$, and $R_6$ have their previous meanings.

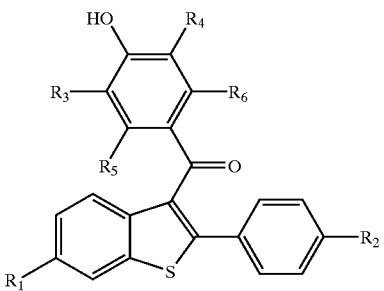

where $R_1$, $R_2$, $R_3$, $R_4$, $R_5$, and $R_6$ have their previous meanings.

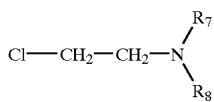

where $R_7$ and $R_8$ have their previous meanings.

Other compounds of formula I where Y is a carbinol or methylene can be prepared in the following manner.

Reduction of the carbonyl to the carbinol and further to the methylene can be accomplished step-wise or form the carbonyl to the methylene in a single step.

Briefly, the carbonyl compound can be reduced to the carbinol with LiAlH$_4$, NaBH$_4$, or the like in appropriate solvents such chlorocarbons, THF, ether, etc. at temperatures of 0–30° C. The carbinol may be reduced to the methylene with silanes, e.g., triethylsilane, in appropriate solvents such as, methylene chloride or THF with a strong acid such as trifluoroacetic acid, at ambient temperatures. Alternatively, the carbonyl compound may be reduced directly to the methylene by using LiAlH$_4$ in a high boiling solvent such as propylbenzene at reflux temperatures.

Sample preparations are listed below and meant for the purposes of illustration and not meant to be limiting in any way.

PREPARATION 1

[2-(4-Hydroxyphenyl)-6-hydroxybenzo[b]thien-3-yl][4-[2-(1-piperidinyl)ethoxy]3-fluorophenyl]methanone Hydrochloride 960 mg (1.85 mmol) of [2-(4-methoxyphenyl)-6-methoxybenzo[b]thien-3-yl][4-[2-(1-piperidinyl)ethoxy]3-fluorophenyl]methanone was dissolved in 30 mL of methylene chloride and cooled to 0° C. and 2.5 g (18.5 mmol) of AlCl$_3$ was added in portions over a 10 minute interval. To the reaction mixture was added 2.75 mL (37 mmol) of EtSH and the reaction was stirred for 15 minutes. The reaction was heated to reflux and allowed to proceed for 1.5 hours. The reaction was allowed to cool and quenched with 100 mL of ice water. The crude product precipitated out and was collected by decanting off the liquids. The solid was dissolved in 50 mL of MeOH and chromatographed on a silica gel column eluted with a solvent of MeOH-CHCl$_3$ (1:9). The appropriate fractions were determined by tlc and combined. The combined fractions were evaporated to dryness in vacuo. The residue was dissolved in 25 mL of MeOH and precipitated by adding a MeOH-HCl solution until no more precipitate formed. The liquid was decanted off and the salt re-dissolved in a minimal amount of MeOH. Ether was then added and the product was allowed to crystallize at −20° C. This yielded 470 mg of the title compound.

PMR: consistent with the proposed structure; MS: m/e= 492 (M-HCl) FD; Exact MS: Calc: 492.1645 Found: 492.1647 $C_{28}H_{27}FNO_4S$.

PREPARATION 2

[2-(4-Methoxyphenyl)-6-methoxybenzo[b]thien-3-yl][4-[2-(1-piperidinyl)ethoxy]3-fluorophenyl]methanone 900 mg (2.20 mmol) of [2-(4-methoxyphenyl)-6-methoxybenzo[b]thien-3-yl][3-fluoro-4-hydroxyphenyl]methanone was dissolved in 12 mL of DMF and 810 mg (4.4 mmol) of 1-(2-chloroethyl)piperidine hydrochloride was added. To the reaction mixture was added 3.3 g (10 mmol) of Cs$_2$CO$_3$ and heated to reflux for one hour. The reaction mixture was filtered to remove the solids. The solvents were removed by evaporation and the residue was chromatographed on a silica gel column eluted with a linear gradient of beginning with CHCl$_3$ and ending with MeOH-CHCl$_3$ (1:19). The desired fractions were determined by tlc, combined, and evaporated to a solid. This yielded 960 mg of the title compound as a tan amorphous solid.

PMR: Consistent with the proposed structure.

PREPARATION 3

[2-(4-Methoxyphenyl)-6-methoxybenzo[b]thien-3-yl][3-fluoro-4-hydroxyphenyl]methanone 500 mg (1.2 mmol) of [2-(4-methoxyphenyl)-6-methoxybenzo[b]thien-3-yl][3-fluoro-4-methoxyphenyl]methanone was dissolved in 6 mL of DMF and 200 mg (2.4 mmol) of NaSEt was added. The reaction was heated to 80° C. for 1.5 hours under a nitrogen atmosphere. The reaction mixture quickly filtered over a silica gel column eluted with CHCl$_3$ to remove the solids and exchange the solvent. The effluent from the column was evaporated to a solid and re-dissolved in EtOAc. The EtOAc solution was chromatographed on a silica gel column eluted with a linear gradient beginning with EtOAc-hexane (3:7) and finishing with EtOAc-hexane (1:1). The appropriate fractions were determined by tlc, combined, and evaporated to dryness. This yielded 200 mg of the title compound as a tan amorphous solid.

PMR: Consistent with the proposed structure.

PREPARATION 4

2-(4-Methoxyphenyl)-6-methoxybenzo[b]thien-3-yl][3-fluoro-4-methoxyphenyl]methanone 5 g (29.4 mmol) of 3-fluoro-4-methoxybenzoic acid was dissolved in 25 mL of thionyl chloride and 3 drops of DMF and heated to reflux for one hour. The reaction mixture evaporated to an oil and used without further purification. The acid chloride was added to 50 mL of dichloromethane and 5.3 g (19.5 mmol) of 2-(4-methoxyphenyl)-6-methoxybenzo[b]thiophene. Over 30 minutes, four portions of AlCl$_3$ (total 16g (120 mmol)) were added and reaction mixture was heated to reflux for several hours. The reaction was quenched by pouring into ice water and the organic layer separated. The organic layer was washed with water and dried by filtration through anhydrous Na$_2$SO$_4$ and evaporated to dryness. The crude product was chromatographed on a silica gel column (HPLC) eluted with a linear gradient beginning with EtOAc-hexane (1:19) and ending with EtOAc-hexane (1:1). The appropriate fractions were determined by tlc, combined, and evaporated to a solid. The product was crystallized out of acetone-ether. This yielded 1 g of the title compound. PMR: Consistent with the proposed structure

PREPARATION 5

[2-(4-Hydroxyphenyl)-6-hydroxybenzo[b]thien-3-yl] [4-[2-(1-piperidinyl)ethoxy]3,5-dimethylphenyl] methanone Hydrochloride 920 mg of the title compound was prepared from 2.9g (5.5 mmol) of [2-(4-methoxyphenyl)-6-methoxybenzo[b]thien-3-yl][4-[2-(1-piperidinyl)ethoxy]3,5-dimethylphenyl] methanone in a manner similar to that in Preparation 1.

PMR: Consistent with the proposed structure; MS: m/e= 502 (M-HCl) FD; Exact MS: Calc: 502.2052 Found: 502.2045 C$_{30}$H$_{32}$NO$_4$S.

PREPARATION 6

[2-(4-Hydroxyphenyl)-6-hydroxybenzo[b]thien-3-yl] [4-[2-(1-piperidinyl)ethoxy]-3-t-butyl-5-methylphenyl]methanone Hydrochloride 620 mg of the title compound was synthesized from 1.3 g (2.3 mmol) of [2-(4-methoxyphenyl)-6-methoxybenzo[b]thien-3-yl][4-[2-(1-piperidinyl)ethoxy]-3-t-butyl-5-methylphenyl]methanone in a manner similar to that of Preparation 1.

PMR: Consistent with the proposed structure; MS: m/e= 543 (M-HCl) FD; Exact MS: Calc: 544.2522 Found: 544.2518 C$_{33}$H$_{38}$NO$_4$S.

PREPARATION 7

[2-(4-Hydroxyphenyl)-6-hydroxybenzo[b]thien-3-yl] [4-[2-(1-piperidinyl)ethoxy]3-chlorophenyl] methanone Hydrochloride 700 mg of the title compound was prepared from 1.3 g (2.42 mmol) of [2-(4-methoxyphenyl)-6-methoxybenzo[b]thien-3-yl][4-[2-(1-piperidinyl)ethoxy]3-chlorophenyl] methanone in a manner similar to that of Preparation 1.

PMR: Consistent with the proposed structure; MS: m/e= 508 (M-HCl) FD; Exact MS: Calc: 508.1349 Found: 508.1360 C$_{28}$H$_{27}$ClNO$_4$S EA: Calc: C, 61.77; H, 5.00; N, 2.57 Found: C, 61.09; H, 5.47; N, 2.34 C$_{28}$H$_{26}$ClNO$_4$S·HCl.

PREPARATION 8

[2-(4-Hydroxyphenyl)-6-hydroxybenzo[b]thien-3-yl] [4-[2-(1-piperidinyl)ethoxy]2-chlorophenyl] methanone Hydrochloride The title compound was prepared from [2-(4-methoxyphenyl)-6-methoxybenzo[b]thien-3-yl][4-[2-(1-piperidinyl)ethoxy]2-chlorophenyl]methanone in a manner similar to that of Preparation 1.

PMR: Consistent with the proposed structure; MS: m/e= 508 (M-HCl) FD; Exact MS: Calc: 508.1349 Found: 508.1355 C$_{28}$H$_{27}$ClNO$_4$S.

PREPARATION 9

[2-(4-Hydroxyphenyl)-6-hydroxybenzo[b]thien-3-yl] [4-[2-(1-piperidinyl)ethoxy]3-cyanophenyl] methanone Hydrochloride The title compound was prepared by dissolving 1.6 g (3.04 mmol) of [2-(4-methoxyphenyl)-6-methoxybenzo[b]thien-3-yl][4-[2-(1-piperidinyl)ethoxy]3-cyanophenyl] methanone hydrochloride in 20 mL of dichloroethane. 2.1 mL of condensed BCl$_3$ was added and sealed in a vessel at room temperature. The reaction was allowed to proceed for sixteen hours. The reaction was quenched by pouring onto ice. The crude product was collected in the organic layer and evaporated to a solid. The product was further purified by chromatography and the hydrochloride prepared as in Preparation 1.

PMR: Consistent with the proposed structure; MS: m/e= 499 (M-HCl) FD; Exact MS: Calc: 499.1629 Found: 499.1703 C$_{29}$H$_{27}$N$_2$O$_4$S.

PREPARATION 10

[2-(4-Methoxyphenyl)-6-methoxybenzo[b]thien-3-yl][4-[2-(1-piperidinyl)ethoxy]3-cyanophenyl] methanone Hydrochloride 1.6 g of the title compound was prepared from 1.45 g (3.49 mmol) of [2-(4-methoxyphenyl)-6-methoxybenzo[b]thien-3-yl][3-cyano-4-hydroxyphenyl]methanone, 1.3 g(7 mmol) of 1-(2-chloroethyl)piperidine, and 4.9 g (15 mmol) of Cs$_2$CO$_3$ in a manner similar to that in Preparation 2.

PMR: Consistent with the proposed structure.

PREPARATION 11

[2-(4-Methoxyphenyl)-6-methoxybenzo[b]thien-3-yl][3-cyano-4-hydroxyphenyl]Methanone 1.45 g of the title compound was prepared from 1.5 g (3.49 mmol) of [2-(4-methoxyphenyl)-6-methoxybenzo[b]thien-3-yl][3-cyano-4-methoxyphenyl]methanone and 590 mg (6.98 mmol) of NaSEt in a manner similar to that in Preparation 3.

PMR: Consistent with the proposed structure;

PREPARATION 12

[2-(4-Methoxyphenyl)-6-methoxybenzo[b]thien-3-yl][3-cyano-4-methoxyphenyl]methanone 1.8 g of the title compound was prepared from 3.9 g (3.9 mmol) of 3-cyano-4-methoxybenzoic acid (converted to the acid chloride with 30 mL of SOCl$_2$ and three drops of DMF), 6 g (22 mmol) of 2-(4-methoxyphenyl)- 6-methoxybenzo [b]thiophene, and 14.7 g (110 mmol) of AlCl$_3$ in a manner similar to that in Preparation 4.

PMR: Consistent with the proposed structure; MS: m/e= 429 (M) FD; EA: Calc: C, 69.91; H, 4.46; N, 3.26 Found: C, 69.65; H, 4.47; N, 3.27 C$_{25}$H$_{19}$NO$_4$S.

PREPARATION 13

[2-(4-Methoxyphenyl)-6-methoxybenzo[b]thien-3-yl][4-[2-(1-piperidinyl)ethoxy]3-chlorophenyl] methanone 2.6 g(8.12 mmol) of 4-[2-(1-piperidinyl)ethoxy]-3-chlorobenzoic acid hydrochloride was dissolved in 25 mL of dichloromethane and 50 mL of SOCl$_2$ with three drops of DMF. The reaction was reluxed for sixteen hours under a nitrogen atmosphere. The reaction mixture was evaporated to dryness, then re-dissolved in 50 mL of dichloromethane. 2.2 g (8.12 mmol) of 2-(4-methoxyphenyl)-6-methoxybenzo[b]thiophene was added to the solution and cooled to 0° C. 7.6 g (56.8 mmol) of AlCl$_3$ was added in three portions to the reaction mixture and allowed to proceed for 1.5 hours. The reaction was quenched by pouring into ice. The organic layer was separated and washed with Na$_2$CO$_3$ solution and with water. The organic layer was dried by filtration through Na$_2$SO$_4$ and evaporated to dryness. The crude material was chromatographed on a silica gel column (HPLC) with a linear gradient beginning with CHCl$_3$ and ending with MeOH-CHCl$_3$ (1:9). The desired fractions were determined by tlc, combined, and evaporated to dryness. This yielded 1.3 g of the title compound as a yellow amorphous foam.
PMR: Consistent with the proposed structure

PREPARATION 14

4-[2-(1-Piperidinyl)ethoxy]-3-chlorobenzoic Acid 7.1 g (35.4 mmol) of 3-chloro-4-hydroxy ethylbenzoate was dissolved in 250 mL of DMF and 13.1 g (71 mmol) of 1-(2-chloroethyl)piperidine hydrochloride and 52 g (160 mmol) of Cs$_2$CO$_3$ was added. The reaction mixture was heated to reflux for four hours. The reaction was allowed to cool and evaporated to dryness. The residue was dissolved in 80 mL of MeOH and 40 mL of 1 N NaOH was added. The reaction mixture was heated to reflux for two hours and cooled to 0° C. The reaction mixture was acidified with 5 N HCl and placed at −20° C. for sixteen hours. The product crystallized out and was filtered off. This yielded 26 g of the title compound as a white powder.

PMR: Consistent with the proposed structure.

PREPARATION 15

[2-(4-Methoxyphenyl)-6-methoxybenzo[b]thien-3-yl][4-[2-(1-pipieridinyl)ethoxy]2-chlorophenyl]methanone 2.5 g (7.81 mmol) of 2-chloro-4-[2-(1-piperidinyl)ethoxy] benzoic acid hydrochloride was dissolved in 50 mL of dichloromethane and 25 mL of SOCl$_2$ and five drops of DMF were added. The reaction mixture was reluxed for sixteen hours under a nitrogen atmosphere. The reaction mixture was evaporated to dryness and triturated twice with CCl$_4$.

2 g (7.5 mmol) of 2-(4-methoxyphenyl)-6-methoxybenzo[b]thiophene was dissolved in 120 mL of dichloromethane and the acid chloride (above) was added. The reaction mixture was cooled to 0° C. and 4.2 g (31.24 mmol) of AlCl$_3$ was added in several portions over a ten minute period. The reaction was allowed to proceed for several hours at 0° C. The reaction was quenched by pouring into ice and the organic layer separated, The organic layer was washed with saturated NaHCO$_3$ solution, water, and dried with Na$_2$SO$_4$. The crude product was chromatographed on a silica gel column eluted with a linear gradient beginning with CHCl$_3$ and ending with CHCl$_3$-MeOH (19:1). This yielded 2.91 g of the title compound as yellow oil.

PMR: Consistent with the proposed structure.

PREPARATION 16

2-Chloro-4-[2-(1-piperidinyl)ethoxy]benzoic Acid Hydrochloride 6 g of the title compound was obtained as a white crystalline powder from 5 g (26.8 mmol) of 2-chloro-4-hydroxy methyl benzoate, 9.9 g (53.6 mmol) of 1-(2-chloroethyl)piperidine hydrochloride and 30 g (108 mmol) of Cs$_2$CO$_3$ in a manner similar to that used in Preparation 14.

PREPARATION 17

[2-(4-Methoxyphenyl)-6-methoxybenzo[b]thien-3-yl][4-[2-(1-piperidinyl)ethoxy]3.5-dimethylphenyl]methanone 2.9 g of the title compound was prepared from 2 g of 2-(4-methoxyphenyl)-6-methoxybenzo[b]thiophene and 4-[2-(1-piperidinyl)ethoxy]-3,5,-dimethylbenzoic acid in a manner similar to that used in Preparation 15.

PREPARATION 18

4-[2-(1-piperidinyl)ethoxy]-3,5,-dimethylbenzoic Acid

The title compound was prepared from 5 g (25.7 mmol) of 3,5-dimethyl-4-hydroxy ethylbenzoate, 18.4 g (100 mmol) of 1-(2-chloroethyl)piperidine hydrochloride, and 49 g (150 mmol) of Cs$_2$CO$_3$ in a manner similar to that used in Preparation 14.

PMR: Consistent with the proposed structure.

PREPARATION 19

[2-(4-Methoxyphenyl)-6-methoxybenzo[b]thien-3-yl][4-[2-(1-piperidinyl)ethoxy]-3-t-butyl-5-methylphenyl]methanone 1.3 g of the title compound (as a tan amorphous powder) was prepared from 2 g (5.62 mmol) of 3-methyl-4-[2-(1-piperidinyl)ethoxy]-5-t-butylbenzoic acid, 1.5 g (5.6 mmol) of 2-(4-methoxyphenyl)-6-methoxybenzo[b]thiophene, and 5.25 g (39.3 mmol) of AlCl$_3$ in a manner similar to that used Preparation 15.

PMR: Consistent with the proposed structure.

PREPARATION 20

3-Methyl-4-[2-(1-piperidinyl)ethoxy]-5-t-butylbenzoic Acid 4.25 g of the title compound (as a white crystalline solid) was prepared from 4 g (16.9 mmol) of 3-methyl-4-hydroxy-5-t-butyl ethylbenzoate, 9.33 g (50.7 mmol) of 1-(2-chloroethyl)piperidine hydrochloride, and 27.7 g (85 mmol) of Cs$_2$CO$_3$ in a manner similar to that used in Preparation 14.

PMR: Consistent with the proposed structure.

The compounds of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, pharmaceutically acceptable salts thus include acetate, phenylacetate, trifluoracetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of additional salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parental administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes. alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

Listed below are formulations for the compounds of formula I. These formulations are given for purposes of illustration and are not intended to limit the scope of this invention in anyway. The term "active ingredient" means a compound of formula I.

| Formulation 1 | |
|---|---|
| Ingredient | Quantity (mg/capsule) |
| Active Ingredient | 0.5–3.0 mg |
| B-cyclodextrin | 0.1 mg |
| DMSO | 1.5 mL |
| Barium Oxide | 0.1 mg |
| Sterile Water | |

A compound of formula I (0.5–3.0 mg) and 0.1 mg of B-cyclodextrin is dissolved in 1.5 mL of DMSO and 0.1 mg of barium oxide is added. The mixture is heated to induce solution (50° C.) and allowed to cool to ambient temperature. Sterile water is added to bring the volume to 2 mL.

| Formulation 2 | |
|---|---|
| Ingredient | Quantity (mg/capsule) |
| Active Ingredient | 0.5–3.0 mg |
| glycerol | 1 mL |
| DMSO | 1 mL |
| Triton X | 0.1 mg |
| Barium Oxide | 0.1 mg |

A compound of formula I (0.5–3.0 mg) is dissolved in 1 mL of DMSO. Triton X (0.1 mg) and barium oxide (0.1 mg) are added along with 1 mL of glycerol. The mixture is thoroughly mixed.

Formulation 3: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

| Formulation 4: Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

| Formulation 5: Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

| Formulation 6: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume. An aerosol solution is prepared containing the following ingredients:

| Formulation 7: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 8: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 9: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

Formulation 10: Combination Capsule I

| Ingredient | Quantity (mg/capsule) |
|---|---|
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 11: Combination Capsule II

| Ingredient | Quantity (mg/capsule) |
|---|---|
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 12: Combination Tablet

| Ingredient | Quantity (mg/capsule) |
|---|---|
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

More generally, the total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

In the examples illustrating the methods, a postmenopausal model is used in which effects of different treatments upon circulating lipids are determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and had ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosina Regimen Tissue Collection.

After a one week acclimation period (therefore, two weeks post-OVX) daily dosing with test compound is initiated. 17α-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis.

Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Data presented in Table 1 show comparative results among ovariectomized rats, rats treated with 17-a-ethynyl estradiol($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to an estrogen is well recognized in the art.

Not only did the compounds of the present invention reduce serum cholesterol compared to the ovariectomized animals, but the uterine weight was only minimally increased. Compared to estrogenic compounds known in the art, the benefit of serum cholesterol reduction without adversely affecting uterine weight is unusual and desirable.

As expressed in the data below, estrogenicity also was assessed by evaluating the response of eosinophil infiltration into the uterus. The compounds of this invention did not cause a large increase in the number of eosinophils observed in the stromal layer of the ovariectomized, rat uteri. $EE_2$ caused a substantial and expected increase in eosinophil infiltration.

The data presented in Table 1 reflect the response of five or six rats per treatment group.

TABLE 1

| Compound No. | Dose mg/kg | Uterine Weight % inch[b] | Uterine Eosinophil (Vmax)[c] | Serum Cholest. % Dec.[d] |
|---|---|---|---|---|
| EE2 | 0.1 | 207.5* | 205.8* | 87.3* |
| 1 | 0.1 | 18.4 | 5.4 | 45.1* |
|  | 1.0 | 14.9 | 4.5 | 59.5* |
|  | 10.0 | 12.5 | 2.7 | 64.1* |

TABLE 1-continued

| Compound No. | Dose mg/kg | Uterine Weight % inch[b] | Uterine Eosinophil (Vmax)[c] | Serum Cholest. % Dec.[d] |
|---|---|---|---|---|
| 5 | 0.1 | −24.4 | 4.0 | 33.8* |
|   | 1.0 | −16.4 | 7.2 | 55.5* |
|   | 10.0 | 27.4 | 25.9* | 74.9* |
| 6 | 1.0 | −35.7 | 2.8 | 55.2* |
| 7 | 10.0 | 46.1* | 30.9 | 62.2* |
| 8 | 10.0 | 37.5* | 12.0 | 42.0* |
| 9 | 10.0 | 16.8 | 7.8 | 38.8* |

[b]Uterine Weight % increase versus the ovarierectomized controls
[c]Eosinphil peroxidase Vmaxium
[d]Serum cholesterol decrease versus ovariectomized controls
*p < .05

An additional demonstration of the method of treating hyperlipidemia due to estrogen deprivation would be the following:

One hundred patients would be chosen, who are healthy post-menopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids.

Fifty women (test group) would receive 60–100 mg of a compound of formula I, e.g., Formulation 1 (above), per day. The other fifty women (control group) would receive a matched placebo per day.

The study is a double-blind design. Neither the investigators or the patients would know as which group each patient is assigned.

A baseline examination of each patient includes serum determination of cholesterol and tri-glyceride levels. At the end of the study period (six months), each patient would have their serum lipid profile taken. Analysis of the data would confirm a lowering of the serum lipids, i.e., cholesterol and/or tri-glycerides, in the test group versus the control.

Uterine Eosinophil Peroxidase (EPO) Assay.

Uteri are kept at 4° C. until time of enzymatic analysis. The uteri are then homogenized in 50 volumes of 50 mM Tris buffer (pH–8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound:

17α-ethynyl estradiol is obtained from Sigma Chemical Co., St. Louis, Mo.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 μL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 μL transferred to triplicate microcultures followed by 50 μL assay medium for a final volume of 200 μL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter.

For example, the compound from Preparation 5, a preferred compound, inhibits proliferation of these cells with an $IC_{50}$ of 40 nM. Fifty percent inhibitory concentration of the test grugs ($IC_{50}$) are determined versus the control (DMSO).

DMBA-Induced Mammary Tumor Inhibition

Estrogen-dependent mammary tumors are produced in female Sprague-Dawley rats which are purchased from Harlan Industries, Indianapolis, Indiana. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Assay 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Assay 2

The same procedure is used as in Test 1, except the period of administration is 6 months.

Assay 3

The same procedure is used as in Test 1, except the period of administration is 1 year.

Assay 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Assay 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Assay 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Assay 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Assay 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Assay 4

A. Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., Exp. Cell Res. 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above assays indicates that the compounds of the present invention are of potential in the treatment of restenosis.

We claim:

1. A compound of the formula (I):

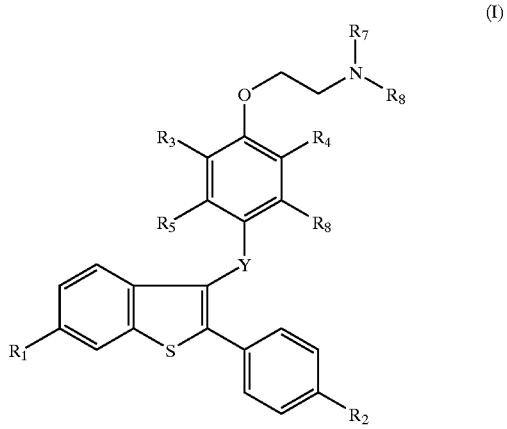

wherein $R_1$ is —H, —OH, —O($C_1$–$C_4$ alkyl), —O—CO($C_1$–$C_6$ alkyl), —OSO$_2$($C_4$–$C_6$ alkyl), or —OCOAr where Ar is optionally substituted phenyl;

$R_2$ is —H, —OH, —Cl, —Br, —($C_1$–$C_4$ alkyl), —OCO ($C_1$–$C_6$ alkyl), —OSO$_2$(C4–$C_6$ alkyl), or —OCOAr where Ar is optionally substituted phenyl,;

$R_3$ is —H, —F, —Cl, —($C_1$–$C_4$ alkyl), —CN, or —O($C_1$–$C_3$ alkyl);

$R_4$ —H, —F, —Cl, —($C_1$–$C_4$ alkyl), —CN, or —O($C_1$–$C_3$ alkyl);

$R_5$ is —H, —F, —Cl, —($C_1$–$C_4$ alkyl), or —O($C_1$–$C_3$ alkyl); and $R_6$ is —H, —F, —Cl, —($C_1$–$C_4$ alkyl), or —O($C_1$–$C_3$ alkyl);

with the provisos that $R_3$, $R_4$, $R_5$ and $R_6$ an not all be hydrogen, and that when one of $R_3$, $R_4$, $R_5$ or $R_6$ is $C_1$–$C_4$ alkyl, no more than two of $R_3$, $R_4$, $R_5$ and $R_6$ can be hydrogen:

Y is —CO—, —CHOH—, or —CH$_2$—;

$R_7$ and $R_8$ are independently $C_1$–$C_4$ alkyl or combine to form, with the nitrogen to which they are attached, 1-piperidinyl, 1-pyrrolidinyl, 1-hexamethyleneimino, or morpholino; or a pharmaceutically acceptable salt thereof.

2. A compound having the name (2-(4-hydroxyphenyl)-6-hydroxybenzo(b)thien-3-yl)(4-(2-(1-piperidinyl)ethoxy)-3,5-dimethylphenyl)methanone or a pharmaceutically acceptable salt thereof.

3. A compound of claim 2 wherein said compound is (2-(4-hydroxyphenyl)-6-hydroxybenzo(b)thien-3-yl)(4-(2-(1-piperidinyl)ethoxy)-3,5-dimethylphenyl)methanone hydrochloride.

4. A compound having the name (2-(4-hydroxyphenyl)-6-hydroxybenzo(b)thien-3-yl)(4-(2-(1-piperidinyl)ethoxy)-3-fluorophenyl)methanone or a pharmaceutically acceptable salt thereof.

5. A compound of claim 4 wherein said compound is 2-(4-hydroxyphenyl)-6-hydroxybenzo(b)thien-3-yl)(4-(2-(1-piperidinyl)ethoxy)-3-fluorophenyl)methanone hydrochloride.

6. A pharmaceutical composition comprising a therapeutically effective amount of a compound according to claim 1 in combination with a pharmaceutically acceptable carrier, diluent or excipient.

7. A method for treating osteoporosis comprising administering to a woman in need of such treatment an effective amount of claim 1; or a pharmaceutically acceptable salt thereof.

8. A method for treating estrogen-dependent cancer comprising administering to a woman in need of such treatment an effective amount of a compound of claim 1; or a pharmaceutically acceptable salt thereof.

9. A method for inhibiting endometriosis comprising administering to a woman in need of such treatment an effective amount of a compound of claim 1.

10. A method for inhibiting aortal smooth muscle cell proliferation comprising administering to a human in need of such treatment an effective amount of a compound of claim 1.

11. A method for inhibiting restenosis comprising administering to a human in need of such treatment an effective amount of a compound of claim 1.

* * * * *